United States Patent [19]

Homma et al.

[11] 3,987,164

[45] Oct. 19, 1976

[54] METHOD FOR PREVENTION OF PSEUDOMONAS AERUGINOSA INFECTIONS

[75] Inventors: Yuzuru Homma; Chiyoji Abe, both of Tokyo; Hiroshi Shionoya, Niiza, all of Japan

[73] Assignees: Yuzuru Homma; Chiyoji Abe; Hiroshi Shionoya, all of Japan

[22] Filed: July 31, 1974

[21] Appl. No.: 493,620

Related U.S. Application Data

[62] Division of Ser. No. 312,212, Dec. 4, 1972, Pat. No. 3,928,565, which is a division of Ser. No. 190,536, Oct. 19, 1971, abandoned.

[30] Foreign Application Priority Data

Oct. 20, 1970 Japan............................... 45-91656

[52] U.S. Cl. ................................................ 424/92
[51] Int. Cl.² ...................................... A61K 39/02
[58] Field of Search ...................................... 424/92

[56] References Cited
OTHER PUBLICATIONS

Homma et al. − J. Bacteriology − vol. 87, (Mar. 1964) pp. 630–640.

Homma et al. − Annals of the N.Y. Academy of Sciences, vol. 133 pp. 508–526 (1966).

Alexander et al. − Surgery Gynecology & Obstetrics − vol. 123 No. 5 (Nov. 1966) pp. 965 to 977.

*Primary Examiner*—Sam Rosen
*Attorney, Agent, or Firm*—Wenderoth, Lind & Ponack

[57] ABSTRACT

The invention involves vaccine preparations comprising cell wall protein component of *Pseudomonas aeruginosa* as active ingredient and a pharmaceutically acceptable carrier. The preparations are suitable for parenteral administration for prophylactic treatment of disease caused by infection of *Pseudomonas aeruginosa*. The cell wall protein component is characterized by the fact that the same exhibits low toxicity and without type-specificity to the variety of antigens of *Pseudomonas aeruginosa*.

2 Claims, 1 Drawing Figure

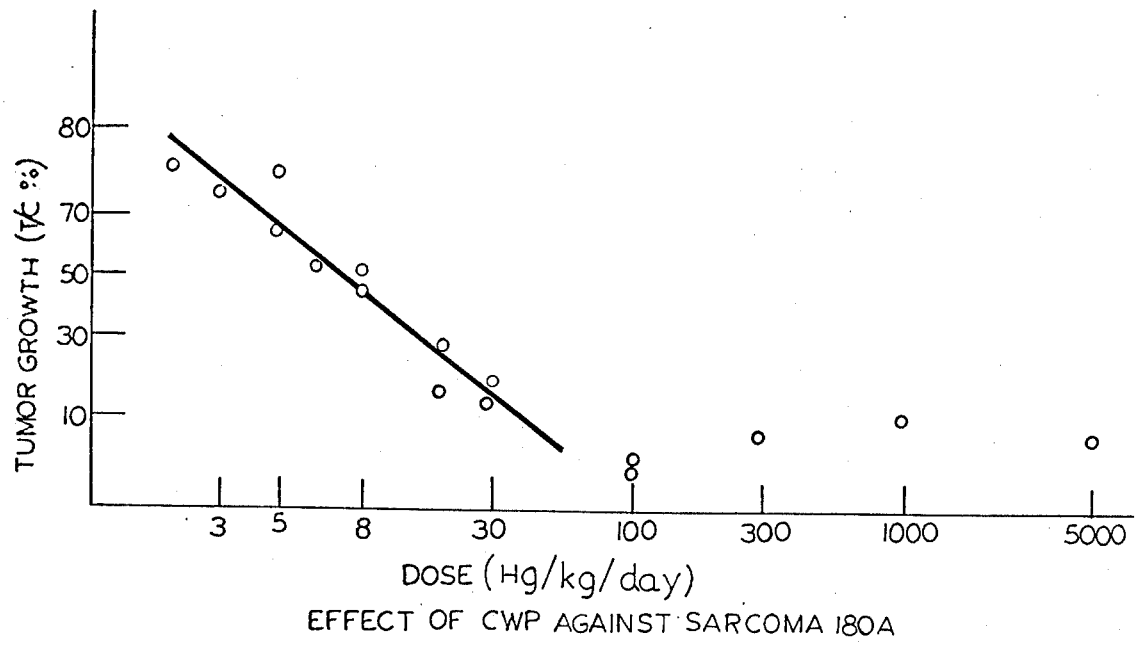
EFFECT OF CWP AGAINST SARCOMA 180A

METHOD FOR PREVENTION OF PSEUDOMONAS AERUGINOSA INFECTIONS

This is a division, of application Ser. No. 312,212, filed Dec. 4, 1972 now U.S. Pat. No. 3,928,565 which is a division of Ser. No. 190,536, filed Oct. 19, 1971, now abandoned.

This invention relates to the pharmaceutical preparation comprising a cell wall component of *Pseudomonas aeruginosa* and a pharmaceutically acceptable carrier. More particularly, the present invention relates to the pharmaceutical composition comprising a cell wall protein component of *Pseudomonas aeruginosa* hereinafter called CWP and a pharmaceutical carrier, which is effective for immunizing animals including man against infection of *Pseudomonas aeruginosa*.

Accordingly, one object of the present invention is to provide vaccine composition in dosage unit form comprising CWP and a pharmaceutical carrier.

Another object of the present invention is to provide a method for immunizing animals and man against infection of *Pseudomonas aeruginosa* by parenteral administration of CWP.

CWP which had first been isolated by J. Y. Homma et al. is a protein antigen existing as a cell wall component of *Pseudomonas aeruginosa* and is also called Original Endotoxin Protein. [J. Y. Homma; J. Bacteriol. 89, pp. 630–640, 1964; Ann. New York Acad. Sci. 133, pp. 508–526, 1966; Zeitschrift fuer Allg. Mikrobiol. 8, pp. 227–248, 1968.]

Because *Pseudomonas aeruginosa*, as it is known, is generally of a natural resistance against usual antibiotics, most of the known antibiotics are ineffective for therapeutical treatment or prevention of disease caused by the infection of *Pseudomonas aeruginosa*.

Amongst bacterial components of *Pseudomonas aeruginosa*, use of Lipopolysaccharide-protein complex (LPS) as a vaccine of *Pseudomonas aeruginosa* is already known. However, the immunizing effect of LPS, as is known, is type specific. LPS vaccine therefore exhibits a selective protection activity only against infection of *Pseudomonas aeruginosa* having the particular Sero-type. The fact is a decisive drawback encountered in the prevention and treatment of disease caused by infection of *Pseudomonas aeruginosa*.

Now the present inventors have found that CWP is an excellent antigen to *Pseudomonas aeruginosa*. It is notable that CWP has almost no type-specificity and exhibits, independent of Sero-type of the bacterium, remarkable effects in therapeutical treatment and in prevention of the infective disease caused by *Pseudomonas aeruginosa*.

Additional advantage of CWP, when administered is its low toxicity and low pyrogenesis that are in a level of about 1/10 of those caused by administration of LPS. Accordingly, CWP is useful for the vaccine of *Pseudomonas aeruginosa*.

Chemical and physical characteristics of CWP vary in a certain extent depending upon sort of the bacterial strain of *Pseudomonas aeruginosa* employed for the production thereof.

In light-absorption spectrum, CWP shows the first peak at 275–280 nm wave length, the second peak at 410–415 nm and the third peak at 550 nm (weak). CWP contains 10–16% of nitrogen; less than 5% of sugars in the term of glucose according to Anthrone method; 0.03–1.7% of amino-sugars; and 0.3–2.0% of phosphorus. The substance belongs to an acid protein having isoelectric point at about pH 4.5 and is sparingly soluble in water and aqueous mineral acids while easily soluble in aqueous alkali. For instance, 1 mg of CWP is completely soluble in 0.1 ml of 1/100 n-NaOH.

In immunochemical study according to the agar gel diffusion test, it has been confirmed that CWP does not contain common antigen to that of LPS.

Acute toxicity ($LD_{50}$) of CWP to mouse, when administered intraperitoneally, was 37.5 mg/kg body weight.

The preparation according to the present invention may be provided in a form of vial or ampoule containing CWP in combination with a pharmaceutically acceptable carrier in dry state. As the pharmaceutical carrier, there may be used glucose, mannitol, carboxymethyl cellulose and the like.

The preparation when used may be dissolved in distilled water for injection or a physiological saline. The solution may be parenterally administered through intramuscular, subcutaneous and intraperitoneal routes. CWP may also be employed with the perfusion techniques.

For the purpose of immunizing man against *Pseudomonas aeruginosa*, it has been found that 3–5 administrations by subcutaneous, intramuscular or inraperitoneal injection of 1–100 µg/day of CWP at the interval of 2–3 days are desirable. For the purpose of therapeutical treatment of patient infected by *Pseudomonas aeruginosa*, administration of a CWP preparation of the present invention may, if necessary, be continued for more than one year without serious side-effects.

The following Examples serve to illustrate the invention.

EXAMPLE 1

Preparation of CWP

Dissociant strain, type 1a, of *Pseudomonas aeruginosa* N 10 was inoculated into 20 liters of the synthetic medium containing 0.5% of glycerol, 2% of sodium glutamate, 0.56% of $Na_2HPO_4\cdot 12H_2O$, 0.025% of $KH_2PO_4$, 0.019% of $MgSO_4\cdot 7H_2O$, 0.001% of $Ca(NO_3)_2$ and 0.000005% of $FeSO_4\cdot 7H_2O$.

Aerobic cultivation of the strain in the abovementioned medium was carried out at 37° C. by passing 0.2 liter of sterilized air per minute per liter of the medium, while pH of the medium was automatically adjusted to 7.4. When the growth entered into a stationary phase, the culture mediu, was incubated for additional three hours, and the incubation was then stopped.

A quantity of toluene was added to autolyse the culture medium. The autolysate was filtered on a filter paper. To the resulting filtrate was added 400 ml of an aqueous 50% zinc chloride solution. The resulting precipitate was recovered by centrifuge. To solubilize CWP, the precipitate was treated with a saturated aqueous solution of $Na_2HPO_4$ and centrifuged off. The supernatant liquor was dialysed against tap water. To the dialysed solution was added sodium acetate at the final concentration of 0.1%. At the temperature of 0° C., six fold (v/v) acetone was added to the solution. The resulting precipitate was collected and dissolved into water. The aqueous solution was subjected to electrodialysis and then lyophilized.

The lyophilized substance was subjected to zone-electrophoresis using a polyvinyl chloride resin as the supporting material in a M/20 borate buffer solution of pH 8.8. As the result of separation, the substance was found to contain two components showing different mobilities under UV-absorption measurement at 280 nm. The fraction corresponding to one component thereof having the lower mobility was dialysed and then lyophilized. The lyophilized substance was dissolved into a 0.01M Tris-HCl buffer solution of pH 8.0 and subjected to a column chromatography on Sephadex G200. A main band thus obtained was collected and adsorbed on a column of DEAE cellulose which had previously been equilibrated with the buffer solution same as that aforementioned. The column was then eluted with the aqueous sodium chloride solutions by means of a gradient procedure.

The fraction eluted with 0.2–0.3M sodium chloride was dialysed and lyophilized. CWP was thus obtained at the yield of 300 mg.

Chemical properties of CWP are as follows:

| | | |
|---|---|---|
| N | 13.8 % | |
| P | 1.1 % | |
| Sugars | 0.01 % | by Anthrone method |
| Amino-sugars | 0.03 % | by Elson-Morgan method |
| Protein | 85 % | by Folin-Ciocalteu method and amino-acid analysis |

A specimen of the bacterial strain of *Pseudomonas aeruginosa* N 10 used in the present invention has been deposited to The Bureau of American Type Culture Collection of U.S.A. under ATCC 21726.

EXAMPLE 2

CWP obtained from the dissociant strain, type 1a, of *Pseudomonas aeruginosa* N 10 was employed in this test. 15 μg of CWP were subcutaneously injected to the respective male mice of D D N strain weighing 25 g in average. On 7th day after the injection, the mice were challenged with the suspensions of *Pseudomonas aeruginosa* N 10 in a 5% hog stomach mucin.

Similar challenge was carried out with *Pseudomonas aeruginosa* 703 which differs from the former with respect to the LPS Sero-type. The results are shown in the following Tables 1 and 2 wherein the numbers of the challenged mice are in the denominators and the numbers of dead mice in the numerators.

Table 1

Strain used to challenge: *Pseudomonas aeruginosa* N 10 (Sero-type 5)

| | Numbers of bacterial cell in 0.5 ml of 0.5 % mucin solution administered IP to immunized mice | | | | |
|---|---|---|---|---|---|
| | $1.5 \times 10^7$ | $1.5 \times 10^6$ | $1.5 \times 10^5$ | $1.5 \times 10^4$ | $1.5 \times 10^3$ |
| Immunized Groups: | 0/5 | 0/5 | 0/5 | 0/5 | 0/5 |
| Control: | 5/5 | 4/5 | 3/5 | 0/5 | 0/5 |

Table 2

Strain used to challenge: *Pseudomonas aeruginosa* 703 (Sero-type 12)

| | Numbers of bacterial cell in 0.5 ml of 0.5 % mucin solution administered IP to immunized mice | | | | |
|---|---|---|---|---|---|
| | $7.5 \times 10^7$ | $7.5 \times 10^6$ | $7.5 \times 10^5$ | $7.5 \times 10^4$ | $7.5 \times 10^3$ |
| Immunized Groups: | 4/4 | 4/4 | 1/4 | 0/4 | 0/4 |
| Control: | — | 2/2 | 4/4 | 4/4 | 0/3 |

From the above Tables, it is recognized that by immunizing with CWP obtained from *Pseudomonas aeruginosa* N 10, it is possible to protect the animals from the challenge of *Pseudomonas aeruginosa* 703 either which possesses LPS Sero-type different from that of the former N 10 strain.

What is claimed is:
1. A method for the prevention of infections caused by *Pseudomonas aeruginosa* which comprises parenterally administering to a human 1 – 100 μg/day of a cell wall protein component produced by aerobic cultivation in an aqueous medium of *Pseudomonas aeruginosa* followed by extraction and purification and having the following properties:
ultraviolet absorption peaks at 275–280 nm, 410–415 nm, and 550 nm (weak);
analysis - 10–16% nitrogen, less than 5% sugars in terms of glucose, 0.03 to 1.7% amino sugars and 0.3 to 2.0% phosphorus;
isoelectric point at about pH 4.5
sparingly soluble in water and aqueous mineral acids, readily soluble in aqueous alkali.
2. A method according to claim 1 wherein the strain of *Pseudomonas aeruginosa* is ATCC 21726, and said component having the analysis
N — 13.8%
P — 1.1%
Sugars (as glucose) — 0.01%
Amino sugars — 0.03%
Protein — 85%.

* * * * *